United States Patent
Nakajima et al.

(10) Patent No.: US 8,144,327 B2
(45) Date of Patent: Mar. 27, 2012

(54) PHOTOACOUSTIC APPARATUS, AND PROBE FOR RECEIVING PHOTOACOUSTIC WAVES

(75) Inventors: Takao Nakajima, Ebina (JP); Kazuhiko Fukutani, Yokohama (JP); Yasufumi Asao, Atsugi (JP); Ryuichi Nanaumi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 65 days.

(21) Appl. No.: 12/548,084

(22) Filed: Aug. 26, 2009

(65) Prior Publication Data

US 2010/0053618 A1 Mar. 4, 2010

(30) Foreign Application Priority Data

Aug. 27, 2008 (JP) ................................. 2008-218104
Aug. 21, 2009 (JP) ................................. 2009-192233

(51) Int. Cl.
  *G01N 21/00* (2006.01)
(52) U.S. Cl. ........ 356/432; 356/439; 356/445; 600/407; 600/459; 600/322
(58) Field of Classification Search .......... 356/439–445; 600/407, 459, 322; 35/439–445
See application file for complete search history.

(56) References Cited

U.S. PATENT DOCUMENTS

| | | | |
|---|---|---|---|
| 2007/0197886 A1* | 8/2007 | Naganuma et al. | 600/322 |
| 2008/0306371 A1 | 12/2008 | Fukutani et al. | 600/407 |
| 2009/0002685 A1 | 1/2009 | Fukutani et al. | 356/72 |
| 2009/0005685 A1* | 1/2009 | Nagae et al. | 600/459 |
| 2009/0198128 A1 | 8/2009 | Fukutani et al. | 600/437 |
| 2010/0049017 A1* | 2/2010 | LeBoeuf et al. | 356/432 |

FOREIGN PATENT DOCUMENTS

JP 2006-208050 8/2006
WO WO 2009/001913 12/2008

OTHER PUBLICATIONS

Niederhauser et al., "Combined Ultrasound and Optoacoustic System for Real-Time High-Contrast Vascular Imaging in Vivo", *IEEE Transaction on Medical Imaging*, vol. 24, No. 4, pp. 436-440 (Apr. 2005).

* cited by examiner

*Primary Examiner* — Gregory J Toatley
*Assistant Examiner* — Iyabo S Alli
(74) *Attorney, Agent, or Firm* — Fitzpatrick, Cella, Harper & Scinto

(57) ABSTRACT

A photoacoustic apparatus obtains information on a specimen by receiving photoacoustic waves which are generated from the specimen resulting from light irradiated to the specimen. The apparatus includes a light source for irradiating light to the specimen, an acoustic wave receiver for receiving the photoacoustic waves, and a light reflection member for causing the light, which is radiated out of the specimen by optical diffusion thereof after having entered an interior of the specimen from the light source, to reenter the interior of the specimen, wherein the light reflection member allows elastic waves to pass therethrough. As a result, a photoacoustic apparatus and a probe are provided which can confine scattered light from the specimen into the specimen, and which can reliably prevent photoacoustic waves from being generated from a receiving element region of the probe by the scattered light.

35 Claims, 13 Drawing Sheets

DISTRIBUTION OF RETURN LIGHT FROM LIVING BODY

LIGHT REFLECTION MEMBER SIZE DEPENDENCY OF LIGHT RELECTION AMOUNT

IN CASE OF n ≦ 1.4

IN CASE OF n > 1.4

PHOTOACOUSTIC APPARATUS, AND PROBE FOR RECEIVING PHOTOACOUSTIC WAVES

BACKGROUND OF THE INVENTION

1. Field of the Invention

The present invention relates to a photoacoustic apparatus which obtains information on a specimen by receiving photoacoustic waves generated from the specimen resulting from light irradiated to the specimen, and it also relates to a probe for receiving the photoacoustic waves.

2. Description of the Related Art

As one of the optical imaging techniques, there has been proposed photoacoustic tomography (PAT) (see a first non-patent document). The photoacoustic tomography is a technique in which a specimen is irradiated with pulsed light generated from a light source, and acoustic waves are detected which are generated from a living body tissue that has absorbed the energy of the light propagated and diffused in the interior of the specimen, whereby those acoustic waves or signals are subjected to analytical processing to visualize the information relevant to optical property values in the interior of the specimen. That is, a photoacoustic effect is a phenomenon in which when pulsed light is illuminated on a material or specimen, an ultrasonic wave (compression wave) is generated due to the cubical expansion of the specimen in a region thereof where the optical absorption coefficient thereof is high. The ultrasonic wave generated due to the cubical expansion of the specimen by irradiating the specimen with pulsed light is called a "photoacoustic wave" in the present invention.

With the above-mentioned technique, an optical property value distribution, especially an optical energy absorption density distribution, in the specimen can be obtained. By using such photoacoustic imaging, an optical property value distribution with a high resolution is obtained.

On the other hand, according to the first non-patent document, it is described that when light is irradiated to a probe surface, a large noise signal will arise which is unrelated to an acoustic signal from the specimen, so an aluminum film, which does not influence the propagation of an ultrasonic wave, is arranged on a front face of a linear array type ultrasonic probe.

[Patent Document 1]
Japanese patent application laid-open No. 2006-208050
[Non-patent Document 1]
Joel J. Niederhauser, et. al., "Combined Ultrasound and Optoacoustic System for Real-Time High-Contrast Vascular Imaging in Vivo", IEEE TRANSACTION ON MEDICAL IMAGING, Vol. 24, No. 4 April 2005

In photoacoustic imaging, there is a problem that it is difficult to obtain information on a deep portion of a specimen because of the attenuation of light due to the optical absorption in a living body. That is, the sound pressure of the acoustic wave obtained is proportional to the amount of local light which reaches an absorber in the specimen. However, the light irradiated to the specimen is rapidly attenuated in the specimen due to the dispersion and absorption thereof. Furthermore, in the case of a human body, a safety restriction on the amount of light allowed to be irradiated thereto is provided by standards, so it is difficult to provide a large amount of light to a deep tissue in the living body. Therefore, it becomes difficult to obtain photoacoustic waves from a deep portion of the living body.

Consequently, according to the extensive study of the present inventors, it has been found that light is strongly scattered in the specimen, so a part of supplied energy is radiated or emitted out of the specimen while not contributing to the generation of a photoacoustic wave. It is considered possible to suppress the loss of the supplied optical energy by reflecting again the diffused light, which has been radiated out of the specimen without being absorbed therein, in a direction of the specimen. Therefore, if effective use of such lost light can be performed, there must be a benefit that information on the deep portion in the living body can be pictured or imaged, or a small-sized light source can be used.

Incidentally, the first patent document includes a suggestion that light is intended to be used effectively by using a light reflection member in the form of a spheroid. In this case, light is irradiated in an effective manner by being converged to the focus of the spheroid before the light is irradiated to the specimen. However, this is not effective use of the diffused light which is the light radiated out of the living body after entering the specimen. In addition, in this case, it is necessary that the specimen should be located at the focus of the spheroid, and a large probe such as an array probe or the like interrupts the light and hence can not be used. Furthermore, a signal is also unable to be detected while scanning the probe. Thus, since large restrictions arise on the use of the technique of this document, the application thereof to general-purpose imaging apparatuses is difficult.

On the other hand, the first non-patent document describes that an aluminum film having such a thickness as not to influence the propagation of ultrasonic waves is arranged between a linear array type ultrasonic probe and a coupling pad made of agar (i.e., gelatin made from seaweed). However, no detailed sizes thereof are indicated. In general, the width of a linear array type ultrasonic probe is about 1 cm and the width of a receiving element thereof is about 5 mm, so the width of the reflecting film arranged on a front face of the probe is at most about 1 cm. In addition, generally, the linear array type ultrasonic probe is provided with an acoustic lens, and takes a convex shape.

According to the study of the present inventors, though details will be mentioned later, even if there was such a reflecting layer or film of a size thus taken so as to be arranged for the purpose of noise removal, the amount of light reflected in the direction of a living body was not necessarily large. In addition, light diffuses when reflected on the plane of reflection of a convex shape, so the energy density of the reflected light irradiated to the living body becomes still smaller. That is, the construction of the first non-patent document can not utilize the optical energy so effectively, and it is formed only for the purpose of noise removal.

As described above, it is considered that a photoacoustic signal from a living body deep portion can be observed by making effective use of the light radiated out of the living body, but any detailed solution to that has not yet been established.

SUMMARY OF THE INVENTION

In view of the problems as referred to above, the present invention has for its object to provide a photoacoustic apparatus, which is capable of making effective use of the energy supplied by causing diffusion light radiated from a specimen to be reflected in a direction of the specimen, and a probe for receiving a photoacoustic wave.

In view of the aforementioned problem, a photoacoustic apparatus of the present invention obtains information on a specimen by receiving photoacoustic waves which are generated from the specimen resulting from light irradiated to the specimen. This photoacoustic apparatus includes a light source for irradiating light to said specimen; an acoustic wave receiver for receiving the photoacoustic waves; and a light reflection member for causing the light, which is radiated out of the specimen by optical diffusion thereof after having entered an interior of the specimen from the light source, to reenter the interior of said specimen; wherein the light reflection member allows elastic waves to pass therethrough.

In addition, a probe of the present invention has an acoustic wave receiver for receiving photoacoustic waves which are generated from the specimen resulting from light irradiated to the specimen. The probe includes a probe main body having a receiving surface arranged in opposition to the specimen; a receiving element for the photoacoustic waves arranged on the receiving surface; and a light reflection member for reflecting the light, which is radiated out of said specimen by optical diffusion thereof after having entered an interior of the specimen; wherein an area of the light reflection member in the receiving surface is set larger than an area of a receiving element region in the receiving surface.

According to the present invention, it becomes possible to cause the light diffused in a living body and radiated out of the living body to reenter the living body under the action of reflection of a reflection member. As a result of this, the efficiency for light utilization is improved, so it becomes possible to make a medical diagnosis at a deeper than conventional position with a limited amount of light.

Other features and advantages of the present invention will be apparent from the following description taken in conjunction with the accompanying drawings, in which like reference characters designate the same or similar parts throughout the figures thereof.

DETAILED DESCRIPTION OF THE EMBODIMENTS

Preferred embodiments of the present invention will now be described in detail in accordance with the accompanying drawings.

In embodiments of the present invention, reference will be made to a biological information imaging apparatus that is constructed as a photoacoustic apparatus which obtains information on an object to be inspected or a specimen by receiving photoacoustic waves which are generated from the specimen resulting from the light irradiated to the specimen, while using the accompanying drawings.

First Embodiment

Fundamental Configuration

Figure 1:
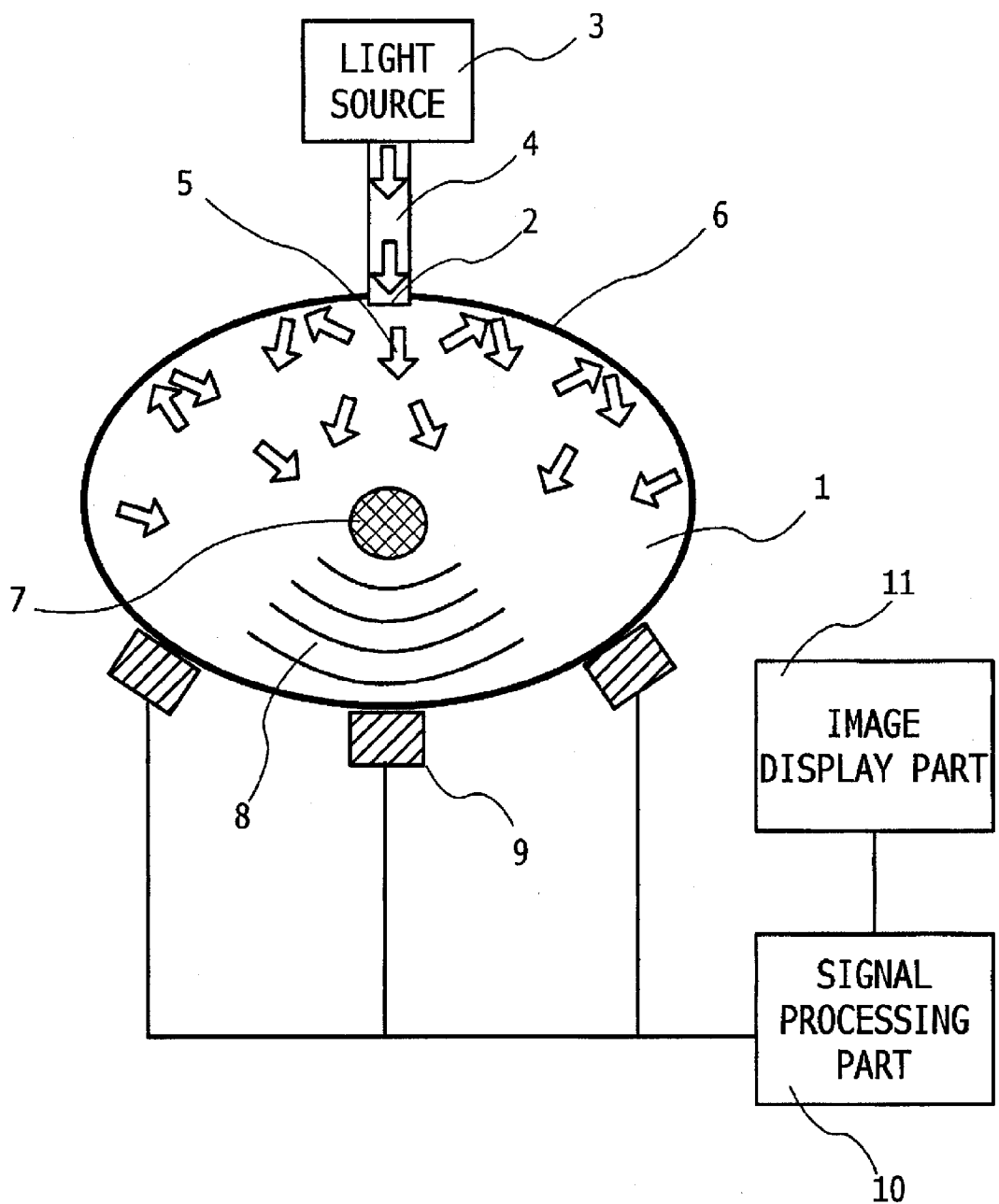
FIG. 1 is a view explaining an example of the construction of an imaging apparatus in a first embodiment of the present invention.

FIG. 1 shows a view explaining an example of the construction of a biological information imaging apparatus in a first embodiment of the present invention. In FIG. 1, a reference numeral 1 denotes a living body as a specimen, 2 a light radiation point, 3 a light source, 4 an optical fiber, 5 light propagating in the living body, 6 a light reflection member, 7 a light absorber, 8 an acoustic wave, and 9 acoustic wave receivers. In addition, the biological information imaging apparatus can include a signal processing part 10 and an image display part 11, which, however, may be provided separately.

The biological information imaging apparatus of this embodiment makes it possible to image the concentration distribution of substances forming a living body tissue obtained from optical property values in the living body and their information for diagnosis of a malignant tumor, a vascular disease, etc., and for the follow-up of a chemical treatment, etc.

The biological information imaging apparatus of this embodiment is provided with the light radiation point 2 at which the living body 1 is irradiated with light. In order to cause light from the light source 3 to be propagated to the light irradiation point 2, the light emitted or irradiated from the light source 3 may be caused to propagate through the optical fiber 4, or in air with the use of a reflector, etc.

In addition, the light 5 incident in the living body is scattered therein, and apart of the light being radiated out of the living body (specimen) is reflected by the light reflection member 6, which is arranged on the periphery of a region to be measured. It is preferable to use, as the light reflection member 6, one which has a reflection factor of 80% or more with respect to the light to be used. For example, in the case of using light in a wavelength range of from 400 nm inclusive to 1,600 nm inclusive as the irradiation light, it is preferable to use the light reflection member 6 formed of aluminum. Alternatively, if irradiation light in a near-infrared region is used, the reflection factor of the light reflection member 6 should be high in that wavelength region, and it is possible to suitably select gold, silver, copper, etc., according to the wavelength used.

If photoacoustic waves, which are elastic waves, are reflected by this reflection member, they will become a cause of artifact. Consequently, it is necessary for the light reflection member to allow the acoustic waves to pass therethrough. In addition, in cases where acoustic waves are detected on the light reflection member, it is indispensable for the light reflection member to reflect the light and at the same time allow the acoustic waves to pass therethrough. A metal material, if used for this, is preferably so thin as to allow acoustic waves to pass therethrough, and for example, an aluminum foil having a thickness of about 10 micrometers is preferable. Also, the transmittance of the elastic waves is preferably not less than 80%, and more preferably, not less than 90%. In addition, a dielectric mirror using a dielectric multilayer film can be used as that which reflects light and allows sound to pass therethrough.

Figure 2:
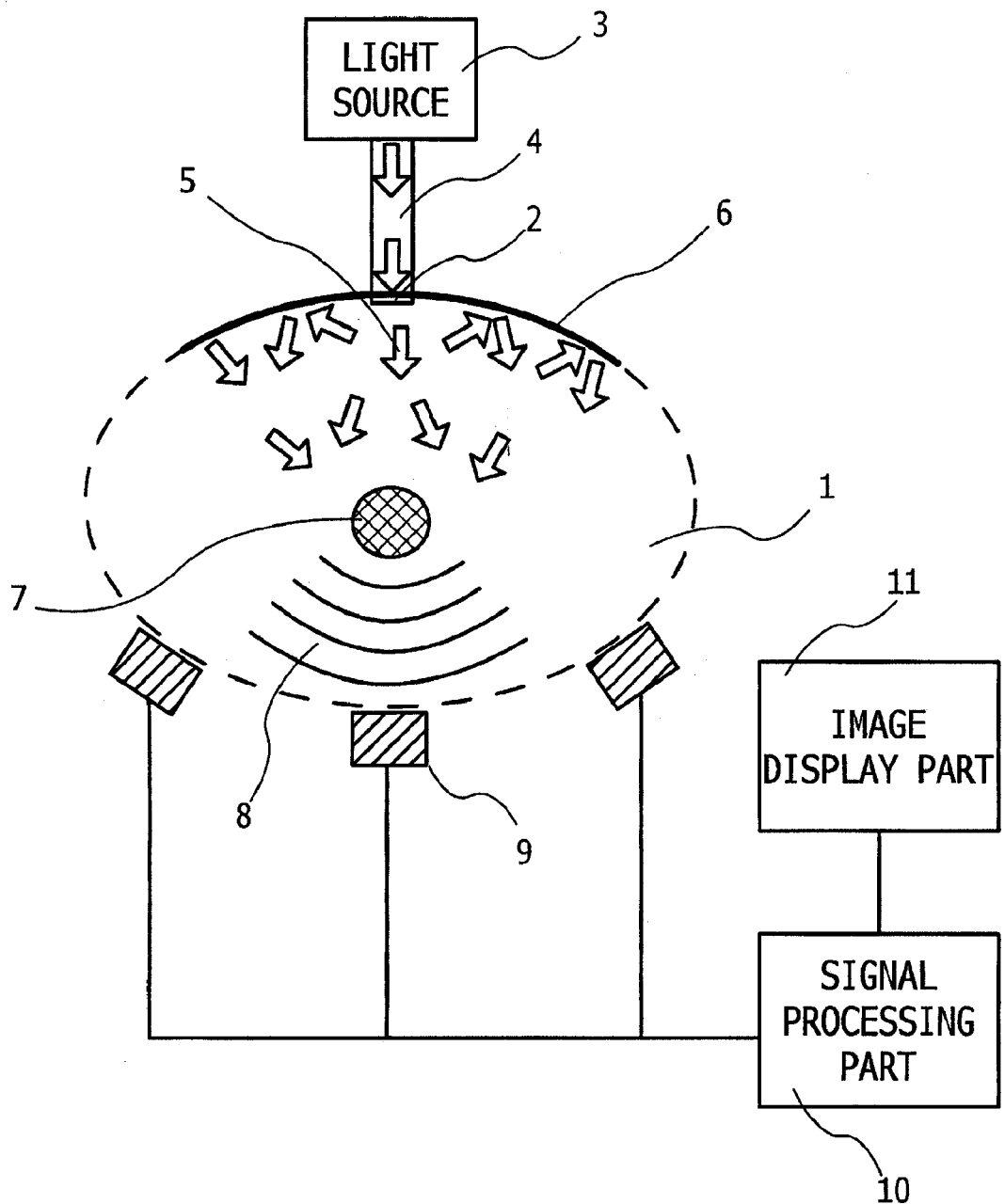
FIG. 2 is a view explaining another example of the construction of the imaging apparatus in the first embodiment of the present invention.

Thus, the light can be confined within the region to be measured by means of the light reflection member selected in this manner, so the amount of light irradiated to the light absorber is increased. In particular, according to the study of the present inventors, as shown in FIG. 2, even the arrangement of the above-mentioned light reflective member 6 on a part of the circumference near the light irradiation point 2 also has a sufficient effect as compared with a conventional construction.

Although the larger the size of this reflective member, the greater the effect becomes, an appropriate size thereof is defined based on the following critical meaning in cases where acoustic waves are detected through the reflective member.

Figure 3:
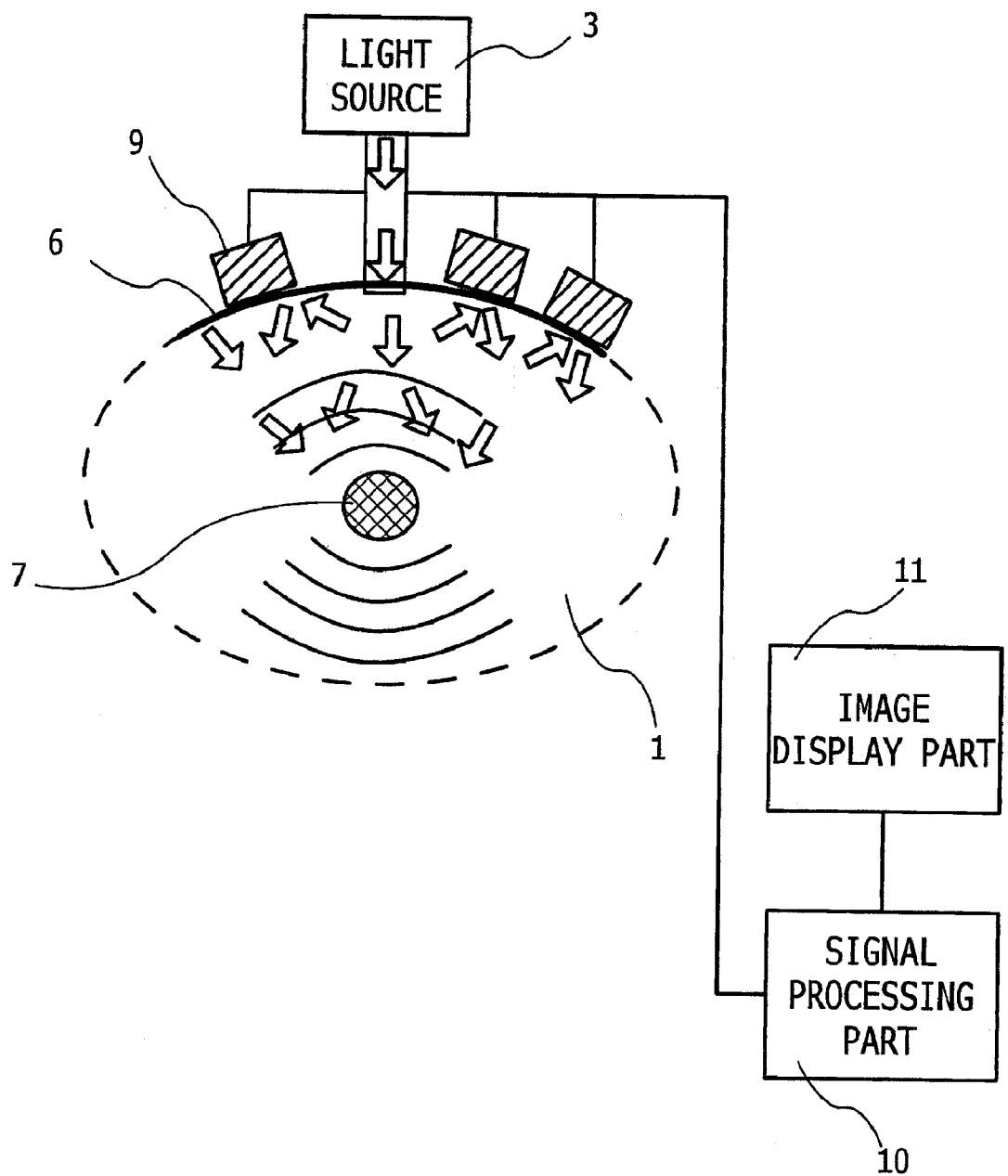
FIG. 3 is a view explaining a further example of the construction of the imaging apparatus in the first embodiment of the present invention.

It is desirable to arrange a light reflection member on a receiving surface of each of the acoustic wave receivers, as shown in FIG. 3, in view of the fact that light can be prevented from entering the acoustic wave receivers and unexpected photoacoustic signals on the surfaces of the acoustic wave receivers and the like can be suppressed. Here, the "receiving surface" in the present invention means a surface on which an actual receiving element in each acoustic wave receiver is arranged. In addition, a region in the receiving surface on which the receiving element is arranged is defined as a "receiving element region".

With respect to the size of the reflection member, in cases where only a part of the receiving element region is covered with the light reflection member, non-uniform distribution of signal strength will arise between the covered part and the remaining uncovered part, or noise will be generated only from the uncovered part. In order to avoid such a phenomenon, it is preferable to cover the entire surface of the receiving element region with the light reflection member. That is, it is preferable that the light reflection member be larger than a receiving element region of a probe.

According to the results of the inventors' study of the various sizes of the light reflection member about the conditions for attaining the purpose of shielding the receiving element region from light in a reliable manner, it is more preferable to cover an area larger by 5 mm or more than each side of the receiving element region with the light reflection member.

Furthermore, at the time when the light radiated out of the living body is caused to return again to the living body by means of the reflection thereof, the light being returned will be spread upon its reflection if the plane of reflection takes a convex shape, as a consequence of which the energy density of the light upon reentering the living body is decreased. Therefore, it is preferable that the light reflection member take a planar shape. In addition, from the point of view of making the energy density higher, it is more preferable that the light reflection member take the shape of a concave mirror, as seen from the specimen side.

Also, it is preferable to arrange something having an optical refractive index larger than the refractive index of the living body, i.e., an optical refractive index of 1.4 or more.

Figure 13A:
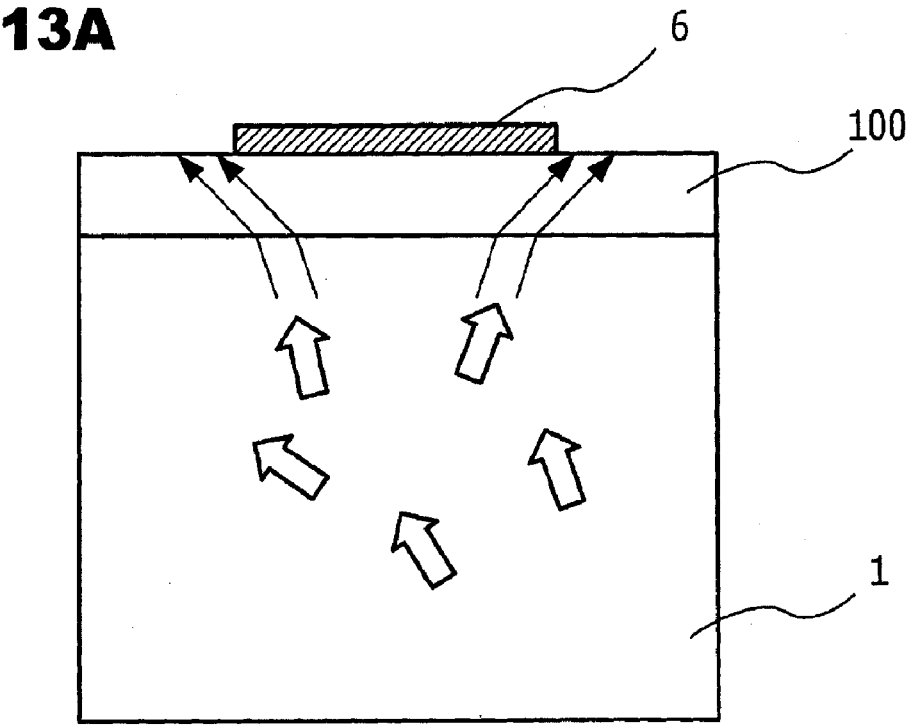
FIGS. 13A and 13B are views explaining the refractive index of a plate-shaped member and the optical path of light emitted from a living body.
Figure 13B:
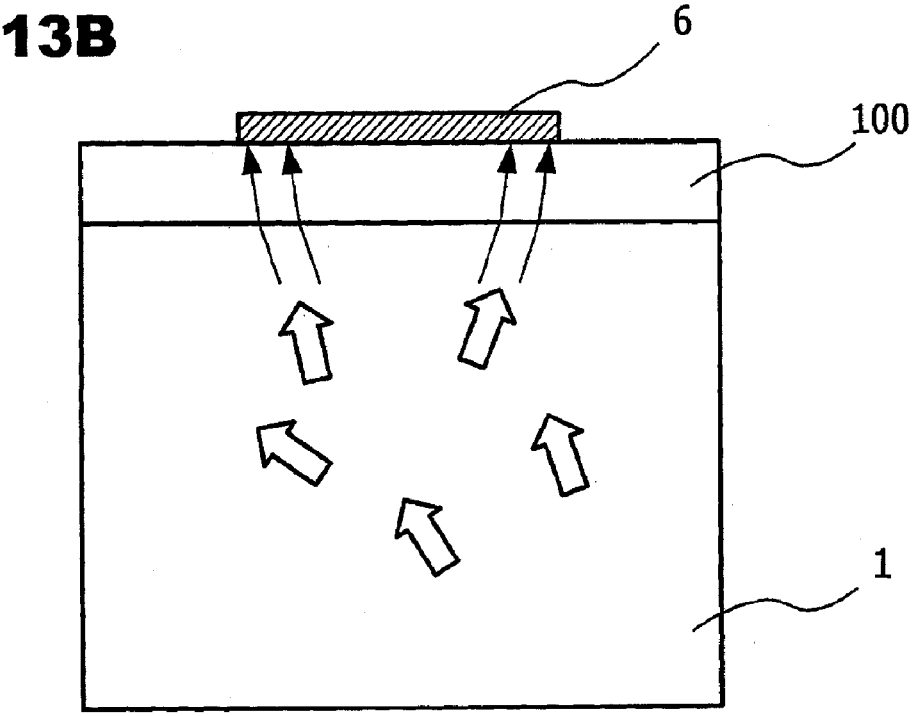

This will be explained below while using FIGS. 13A and 13B. A reference numeral 100 denotes a plate-shaped member that is able to be in contact with the living body 1. The plate-shaped member is arranged between the light reflection member and a light irradiation region to the living body. The refractive index of the living body 1 is generally 1.37-1.4. Now, consideration will be given to refraction by the plate-shaped member which is arranged between the light reflection member 6 and the living body 1. The refractive index of general ultrasonic gel or a coupling pad made of agar given in the aforementioned first non-patent document is generally equivalent to the refractive index of water, and hence is about 1.33. In this case where a member having a refractive index smaller than the refractive index of the living body is in contact with the living body, the emitting angle of the light radiated from the living body becomes large, as shown in FIG. 13A, the light which does not reach the reflector of a limited area increases. On the other hand, in cases where a member having a refractive index larger than the refractive index of the living body is in contact with the living body, as shown in FIG. 13B, the radiation angle of the light radiated from the living body becomes small, so the amount of light which reaches the reflector can be increased.

Also, it is preferable, due to the same reason as the above-mentioned light reflection member, that the plate-shaped member 100 has a property to allow an acoustic wave to pass therethrough. As such a substance, it is possible to use polymethylpentene which has a refractive index of 1.463 and in which sonic waves attenuate less.

Figure 5:
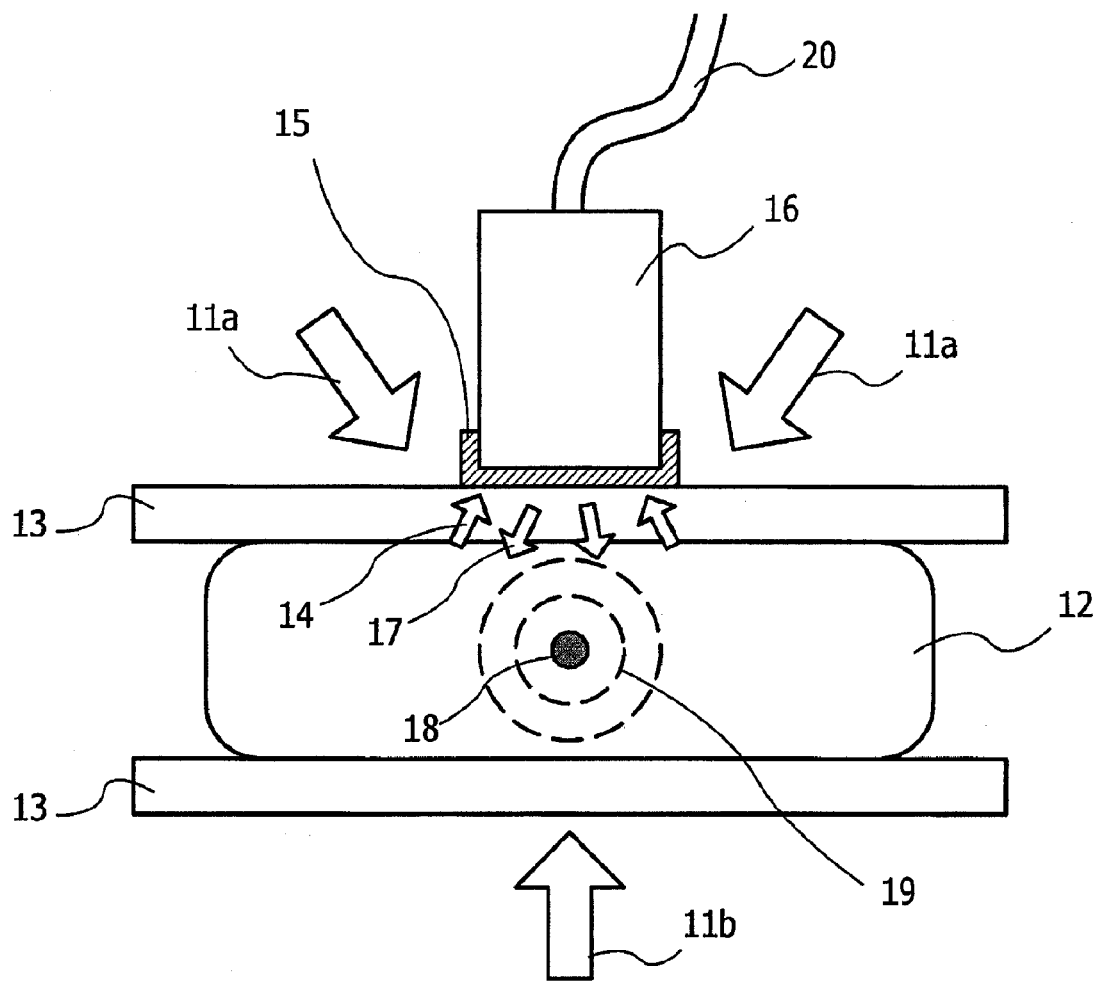
FIG. 5 is a view explaining an example of the construction of a biological information processing apparatus in a second embodiment of the present invention.

In addition, in this embodiment, as shown in FIG. 5 or the like, it is preferable that the light reflection member be arranged in such a manner that an orthogonal projection of the light reflection member onto the light irradiation region to the specimen has a region which overlaps with the light irradiation region. Here, "the light irradiation region to the specimen" means an irradiation (emission) region of light in a part where the photoacoustic apparatus of the present invention is able to be in contact with the specimen when the light is irradiated to the specimen. That is, when the specimen is in contact with the photoacoustic apparatus, the irradiation region will be in match with alight irradiated area in the specimen. By taking the construction as described above, it is possible to cause diffused light from a region in which the diffused light tends to emit out of the specimen to be intensively reflected into the specimen.

In addition, the biological information imaging apparatus of this embodiment is provided outside the living body with the acoustic wave receivers 9 that detect the photoacoustic waves 8 generated by a tumor or a blood vessel in the living body or the light absorber 7 similar to these in the living body due to the absorption of a part of the energy of light, and converts them into corresponding electric signals, respectively. In addition, the biological information imaging apparatus is further provided with the signal processing part 10 that obtains optical property value distribution information through the analysis of the electric signals.

The light irradiation point 2 is used as a device or unit to irradiate the light of a specific wavelength to be absorbed by a specific component among those components which make up the living body. The light source 3 is assumed to be a light source that generates pulsed light. It is preferable that the pulsed light is on the order of from several nanoseconds to hundreds of nanoseconds, and the wavelength thereof is in a range of from 400 nm inclusive to 1,600 nm inclusive. Laser is preferable as the light source 3, but it is also possible to use a light emitting diode or the like, instead of laser.

As a laser, there can be used various types of lasers such as a solid-state laser, a gas laser, a dye laser, a semiconductor laser, and the like. If dyes or OPO (Optical Parametric Oscillators) having convertible oscillating wavelengths are used, it will also become possible to measure differences between optical property value distributions due to the wavelengths. With respect to the wavelength of the light source to be used, it is preferably in a range of from 700 to 1,100 nm, in which the absorption of optical energy in the living body is small. In addition, the absorption of optical energy in the light absorber 7 is increased due to the confinement of light, so it is possible to use a wider wavelength range than the above-mentioned one, such as for example a range of from 400 to 1,600 nm, too.

The acoustic wave receivers 9 of this embodiment detect the photoacoustic waves generated from the light absorber in the living body which has absorbed a part of the energy of the light irradiated to the living body from the light irradiation point, and convert them into electric signals, respectively. As such an acoustic wave receiver 9, there can be used any type of acoustic wave detector such as a transducer using a piezoelectric phenomenon, a transducer using the resonance of light, a transducer using the change of capacitance, and so on as long as an acoustic wave signal can be detected. Since it is known that the transducer for detecting the change of capacitance can be easily designed as an element of a wide band, such a transducer is desirable in that it can detect ultrasonic waves from absorbers of various sizes.

Although in this embodiment, there has been shown the case in which the plurality of the acoustic wave detectors are arranged on the surface of the living body or with the light reflection member interposed therebetween, the present invention is not limited to such arrangements, but can be constructed such that acoustic waves can be detected at a plurality of locations. That is, since the same effect will be obtained if acoustic waves can be detected at the plurality of locations, one acoustic wave detector can be scanned on the living body surface or on the light reflection member. In addition, it is a preferable embodiment of the present invention that one acoustic wave detector is caused to scan along the above-mentioned plate-shaped member 100. Thus, as a movable part (movable mechanism) for causing the acoustic wave receiver to scan, there is recited a slider or the like which serves to support a probe including an acoustic wave receiver and to move this probe, but the present invention is not limited to this. Here, note that in cases where an electric signal obtained from each acoustic wave detector 9 is small, it is preferable to amplify the strength of the signal by the use of an amplifier. Also, it is desirable to use an acoustic impedance matching agent for suppressing the reflection of sonic waves, which is arranged between each acoustic wave detector and a biological substance or living body which is an object to be measured. In the case of the provision of the plate-shaped member 100, it is preferable to arrange the acoustic impedance matching agent at least between the plate-shaped member 100 and the living body. In this case, the construction is such that the plate-shaped member 100 is able to be in contact with the living body through the matching agent.

The signal processing part 10 of this embodiment analyzes the above-mentioned electric signals, whereby optical property value distribution information on the above-mentioned living body can be obtained. For example, as shown in FIG. 1, the signal processing part 10 calculates, based on the electric signals obtained from the acoustic wave detectors 9, optical property value distribution such as the position and size of the absorber in the living body, the optical absorption coefficient thereof, or the optical energy accumulation distribution thereof. Here, note that as the signal processing part 10, there may be used anything that can store the strength of the acoustic waves 8 and the temporal change thereof, and convert or transform them into the data of optical property value distribution by means of a computing unit. For example, there can be used an oscilloscope and a computer or the like which is able to analyze data stored in the oscilloscope.

Second Embodiment

Probe

Next, reference will be made to another embodiment of the present invention in which a construction example of the above-mentioned probe that can realize effective use of light and a biological information processing apparatus using such a probe, while using the accompanying drawings. In this embodiment, it is featured that a light reflection member is provided on a probe which includes an acoustic wave receiver. FIG. 5 illustrates a view explaining the construction example of the biological information processing apparatus in this embodiment.

The biological information processing apparatus of this embodiment makes it possible to image optical property values in a living body and the concentration distribution of substances that constitutes the living body tissue obtained from the information of these, for diagnosis of a malignant tumor, a vascular disease, etc., and for the follow-up of a chemical treatment, etc.

The biological information processing apparatus of this embodiment irradiates a living body 12 with irradiation lights 11a, 11b. The living body 12 is fixed with an immobilization device (plate-shaped member) 13. Although the lights 11a, 11b are irradiated from opposite sides in FIG. 5, either one of these lights 11a, 11b may be irradiated from one side.

In addition, in a receiving element region of a probe 16, there is arranged a light reflection member 15 that reflects light 14 radiated out of the living body after the lights 11a, 11b having entered the interior of the living body diffuse therein. With such an arrangement, the light 14 radiated out of the living body is caused to reenter the interior of the living body, as shown by arrows 17. It is preferable that the reflection factor of the light reflection member 15 be not less than 80% in the light to be used. For example, in cases where light in a wavelength range of from 400 nm inclusive to 1,600 nm inclusive is used as irradiation light, it is preferable to use the light reflective member 15 formed of aluminum.

Alternatively, if irradiation light in a near-infrared region is used, the reflection factor of the light reflection member should be high in that wavelength region, and it is possible to suitably select gold, silver, copper, etc., according to the wavelength used. Silver is particularly effective because it has a reflection factor of not less than 90% in both a visible light region and a near-infrared light region.

In the biological information processing apparatus of this embodiment, in order to detect acoustic waves in the receiving element region, the light reflection member needs to reflect the light and at the same time to allow acoustic waves to pass therethrough, and hence metal, being so thin as to allow acoustic waves to pass therethrough, for example, an aluminum foil having a thickness of about 10 micrometers, is preferable. In addition, a dielectric mirror using a dielectric multilayer film can be used as that which reflects light and allows sound to pass therethrough.

Figure 6A:
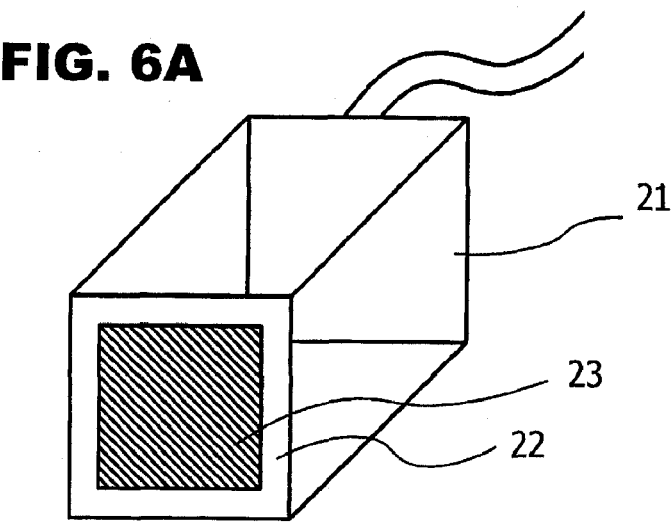
FIGS. 6A through 6E are views explaining probe main bodies in the second embodiment.
Figure 6B:
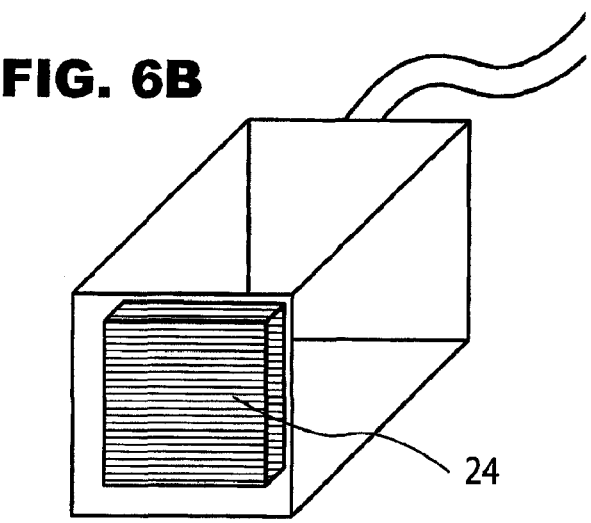
Figure 6C:
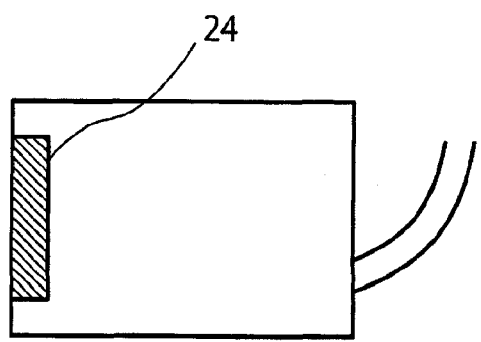
Figure 6D:
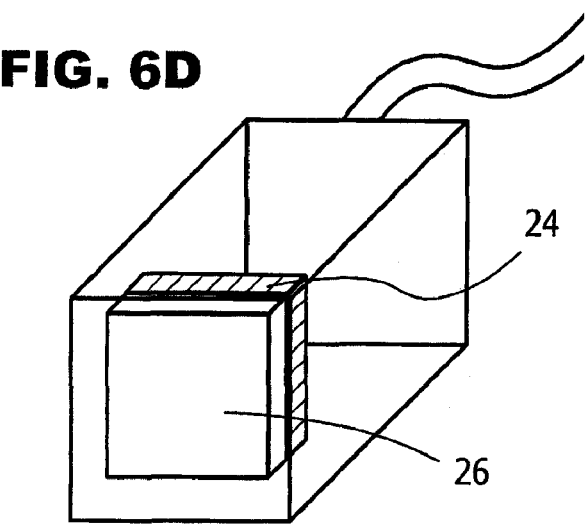
Figure 6E:
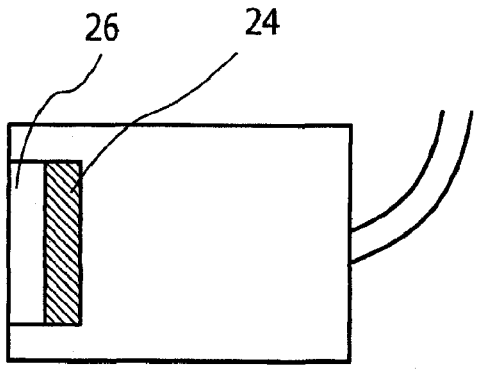

Here, the arrangement of the light reflection member 15 will be described while using FIGS. 6A through 6E and FIGS. 7A through 7F. First, a probe will be explained by using FIGS. 6A through 6E. In FIG. 6A, a receiving surface is a surface 22 of a probe main body 21 on which a receiving element is arranged. This receiving surface is placed in opposition to a specimen at the time of measurement. The receiving surface of the probe includes two cases; a receiving element 24 is arranged on the probe receiving surface in an exposed or uncovered state (FIGS. 6B and 6C), or an acoustic impedance matching layer 26 is arranged in front of a receiving element 24 (FIGS. 6D and 6E). A receiving element region in either of these cases is a region denoted at 23 in FIG. 6A. That is, in the case of the provision of the matching layer, the matching layer is also included in the receiving element region.

Figure 7A:
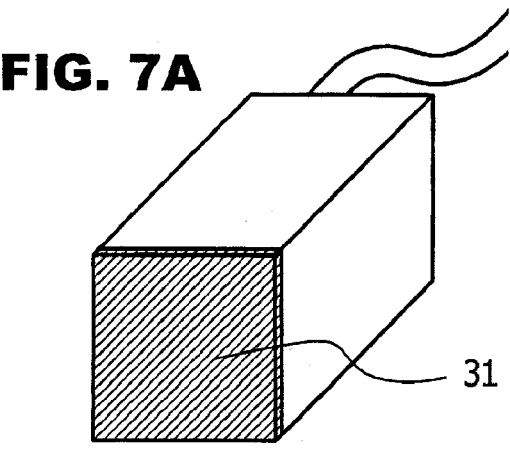
FIGS. 7A through 7F are views explaining probes in the second embodiment.
Figure 7B:
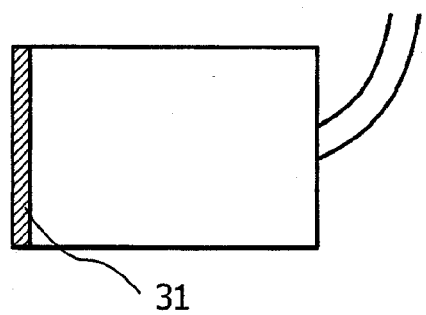

Three types of arrangements of the light reflection member are shown in FIGS. 7A through 7F. FIGS. 7A and 7B show the first type of arrangement. FIG. 7A is a perspective view and FIG. 7B is a plain view thereof. In FIGS. 7A and 7B, a light reflection member 31 has an area which is set larger than the area of the receiving element region (23 in FIG. 6A). In addition, the light reflection member 31 is formed so as to cover the entire surface of the receiving surface 22. Since the area of the light reflection member 31 on a measuring plane of the probe is set larger than the area of the receiving element region on that measuring surface, it is possible to prevent scattered light from being irradiated to the receiving element in a reliable manner. As a result, it becomes possible to obtain more accurate information on the interior of the specimen.

Figure 7C:
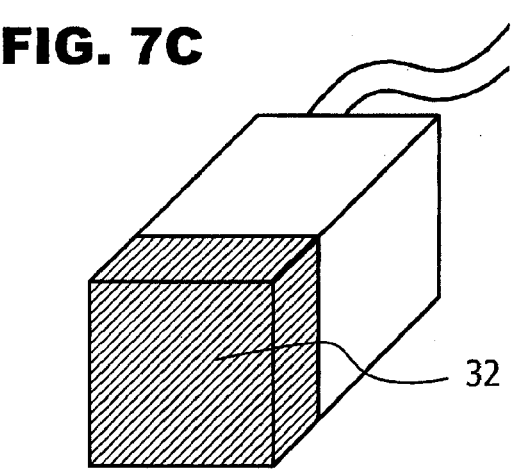
Figure 7D:
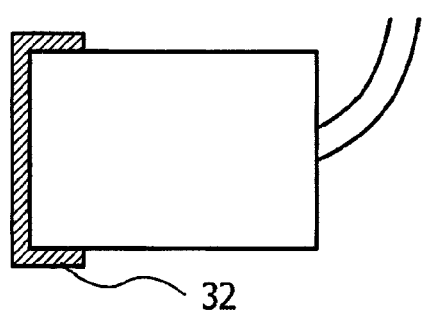

FIGS. 7C and 7D show the second type of arrangement of the light reflection member. FIG. 7C is a perspective view and FIG. 7D is a plain view thereof. In FIGS. 7C and 7D, a light reflection member 32 covering the entire surface of the receiving surface 22 is extended to the side faces of the probe main body 21. That is, the light reflection member 32 is arranged on part of the side faces of the probe main body 21, i.e., the side faces of the probe around its measuring plane. In the case of FIG. 7A, in cases where a little amount of gap, etc., occurs in the adhesion of the reflection member to the receiving region, even a slight amount of light may come in therefrom so that a photoacoustic wave can be generated in the receiving region. Thus, by surrounding the periphery of the probe, as shown in FIG. 7C, the invasion of light can be prevented thoroughly, and also a small amount of photoacoustic wave produced from the periphery of the probe can also be prevented. From such a reason, the arrangement of FIG. 7C is larger in the effect of reducing the noise of photoacoustic waves than that of FIG. 7A.

Figure 7E:
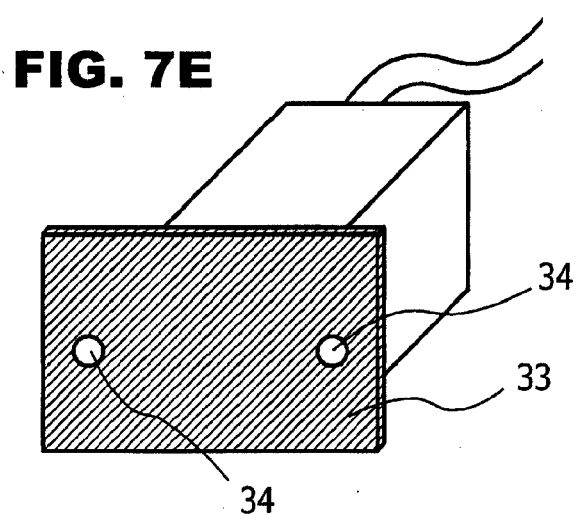
Figure 7F:
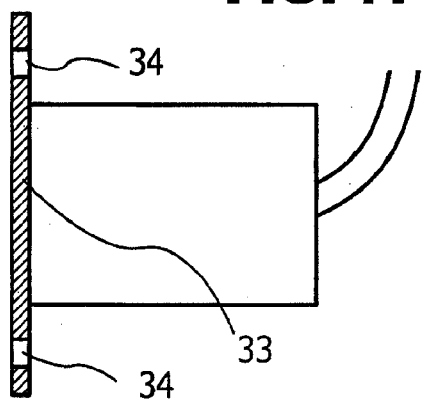

FIGS. 7E and 7F show the third type of arrangement of the light reflection member. FIG. 7E is a perspective view and FIG. 7F is a plain view thereof. In FIGS. 7E and 7F, a reflection member 33 has an area larger than that of a receiving region of a probe, and has apertures 34 formed in a part thereof for allowing light to pass therethrough. It is preferable that light be introduced from a side face of the probe by the use of an optical fiber, and caused to pass through the apertures 34. In this case, the diameter of the apertures 34 becomes equal to the diameter of the optical fiber. By taking such an arrangement, the light being diffused and radiated out of the living body can be more efficiently confined in a specimen, thereby making it possible to obtain a wider range of optical information. At the same time, it is also possible to prevent the light incident to the receiving region. In addition, it is preferable that a material having a light refractive index of 1.4 or more to allow ultrasonic waves to pass therethrough be arranged between the above-mentioned light reflection member and the specimen, as described above. This material can also be used as an immobilization device for the specimen.

(Relation Between the Size and the Reflective Effect of the Reflection Member)

Figure 8:
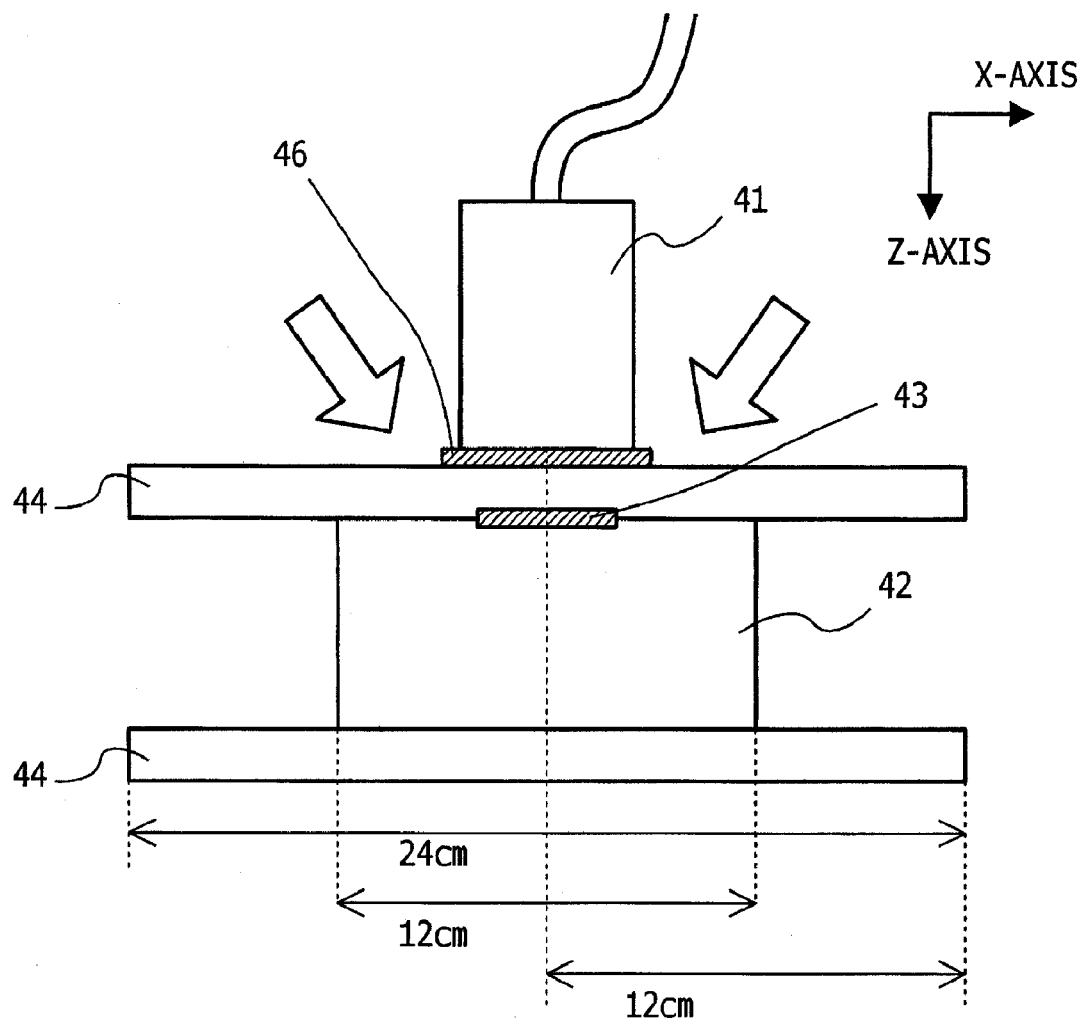
FIG. 8 is a view explaining a simulation model in the second embodiment of the present invention.

Here, a simulation was performed in order to investigate the relation between the size of a light reflection member, and the effect of reflecting the diffused light radiated from a specimen and returning it to the specimen. The simulation was carried out with a model, as shown in FIG. 8.

The size of a receiving element region of a probe 41 was set as a square of 4 cm×4 cm. The irradiation of light to a specimen 42 was performed only from a probe side. This is because in this construction, the light irradiated from a side opposite to the probe side is greatly attenuated in the specimen 42, and hence the amount of light reaching the reflection member is itself small and its contribution to the reflection effect is also small. Also, the light irradiation was performed in such a manner that a light irradiation region 43 similarly becomes a square of 4 cm×4 cm on a surface of the living body. The amount of light irradiated was set to 1 W, and the density of light irradiation on an irradiation surface was set to be constant. The thickness of the specimen 42 in a direction of z was 4 cm; the size thereof was a square of 12 cm×12 cm; the refractive index thereof was set to 1.333; the optical absorption coefficient pa thereof was set to 0.1 $cm^{-1}$; and the effective light scattering coefficient thereof was set to 10 $cm^{-1}$. In addition, the thickness of an immobilization device 44 was 1 cm; the size thereof was a square of 24 cm×24 cm; and the refractive index thereof was set to 1.463.

Figure 9A:
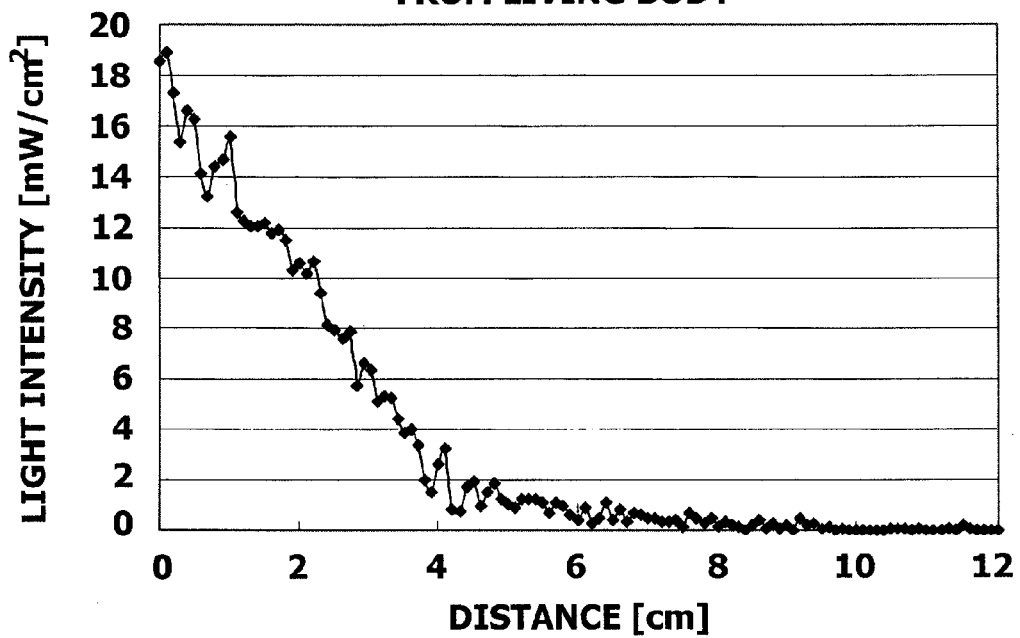
FIGS. 9A and 9B are graphs which plot simulation results, respectively, in the second embodiment of the present invention.

The behavior of the light irradiated to the specimen under such conditions was simulated by means of Monte Carlo method. FIG. 9A shows the result of a simulation without the reflection member being arranged, and plotted therein is the intensity of the diffused light radiated from the specimen 42 measured at the position denoted by numeral 46 where the reflection member should be arranged in reality. In this figure, the direction of the x axis (distance) is taken as shown in FIG. 8, and the origin is set to the center of the receiving region of the probe 41. For example, the size of the receiving region is a square of 4 cm×4 cm, so in this graph, an end of the receiving region becomes a position of x=2 cm.

Figure 9B:
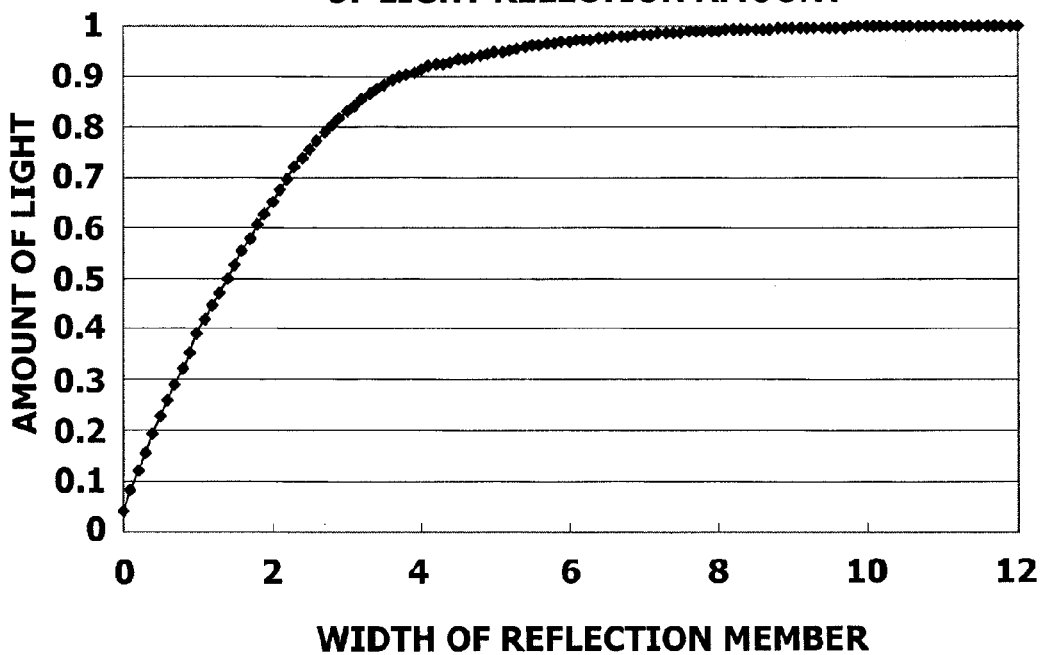

FIG. 9B illustrates the result of integrating the light amount distribution of FIG. 9A in the direction of the x axis. That is, this result shows the relation between a size of a region, and a sum total of the amounts of the diffused light radiated from that region. Here, when the value of x is 12 cm, it becomes an entire range of the simulation, and the amount of light of the diffused light radiated from this range becomes a total amount of light radiated from the entire specimen. For this reason, the value of the amount of light is standardized with the value thereof at x=12 cm being taken as 1. For example, the total amount of light radiated out of the specimen from a square region of 4 cm×4 cm identical to that of the receiving region is indicated at a place whose x axis in this graph is 2 cm, and becomes 65% of the total amount of light radiated from the entire specimen.

If a reflection member having a reflection factor of 100% is arranged in this range, all the diffused light radiated from this range can be reflected. This indicates that if a light reflection member having a reflection factor of 100% and a square size of 4 cm×4 cm identical to the size of the receiving region is arranged, 65% of the diffused light radiated from the specimen 42 can be returned to the specimen 42, whereby the effective use of the diffused light can be made.

From FIG. 9B, it is found that in order to return 80% of the amount of light radiated from the specimen 42 to the specimen 42, a value of 2.8 cm on the x axis of the graph, i.e., a reflection member having a square shape of 5.6 cm×5.6 cm, is required. On the other hand, it is also understood that even only if a value of 1 cm on the x axis of the graph, i.e., a reflection member having a square shape of 2 cm×2 cm is arranged, about 40% of the diffused light can be to the specimen 42.

Here, note that in the reflection member having a width of less than 1 cm as suggested in the aforementioned first non-patent document, the value on the x axis is less than 0.5 cm, so it is found that only less than 20% of the total amount of light radiated can be returned. From the above simulation results, it can be seen that the larger the area of the reflection member, the more effectively the diffused light radiated from the specimen can be returned to the specimen.

Considering the result of the light reflection efficiency and the effect of preventing the generation of photoacoustic waves due to the irradiation of the diffused light to the receiving element region in a reliable manner, it is understood that it is effective to use a reflection member with a size larger than the receiving element region.

In addition, according to the above-mentioned simulation, though it is effective that the shape of the reflection member has a wide width, in cases where a probe is of a so-called 1D (one dimensional, linear) type, its reflection member becomes narrow in width, as in the aforementioned second non-patent document. Alternatively, in the case of the 1D type probe, a reflection member having a shape quite different from that of the probe should be adopted, which is not desirable from the viewpoint of practical use. Therefore, as for the probe used for the present invention, it is preferable to use a so-called 2D (two dimensional) array type probe. The adoption of the 2D array type probe serves not only to improve the efficiency of reflective light, but also to make the probe and the reflection member substantially similar in shape to each other, so it is preferable from a handling point of view or from a design point of view.

By means of the light reflective member thus selected and arranged which is larger than the area of the receiving element region on the measuring plane, it is possible to efficiently prevent the light irradiated into the specimen from being radiated out of the living body without being absorbed in the specimen. As a result, in cases where the specimen is the living body, it becomes possible to cause a larger amount of light to be absorbed by a tissue which is wanted to be inspected, without wasting the irradiation light. Also, according to this, strong light can be made to reach even a deep portion of the specimen, so a wide range of optical characteristic value distribution in the deep portion in the living body can be imaged. Furthermore, it becomes possible to image the optical property of a living body tissue by using a wavelength range other than the near-infrared region in which the light in the living body is strongly absorbed, i.e., is liable to be attenuated. In addition, it is possible to prevent the scattered light from being irradiated to the receiving element region in a reliable manner. Accordingly, the generation of photoacoustic waves from the receiving element region can be prevented in a reliable manner, and noise other than signals from the specimen can be reduced. Thus, by using the probe provided with the above-mentioned light reflection member, it becomes possible to acquire more accurate images with less noise in a wide range up to the deep portion of the living body.

Although in FIG. 5, the living body 12 is fixed by means of the immobilization device 13, it does not necessarily need to take such a construction. That is, it is also possible to use the probe 16 by directly pressing it against the living body 12. In this case, the light reflection member 15 will be in contact with the living body 12.

The probe 16 detects an acoustic wave 19 generated by a tumor, a blood vessel in the living body or a light absorber 18 in the living body similar to these due to their absorption of a part of the energy of light, and converts it into a corresponding electric signal. This electric signal is sent to a signal processing part through a signal transmission part 20. In the signal processing part, the electric signal thus transmitted is analyzed, whereby optical property value distribution information on the above-mentioned living body can be obtained. For example, the signal processing part calculates, based on the electric signal obtained from the probe 16, optical property value distribution such as the position and size of the absorber in the living body, the optical absorption coefficient thereof, or the optical energy accumulation distribution thereof.

Here, note that in the case of using light of a plurality of wavelengths, optical coefficients in the living body are calculated with respect to the individual wavelengths, respectively. Then, by comparing those values with wavelength dependency specific to substances (glucose, collagen, oxidized and reduced hemoglobin, etc.) which constitute the living body tissue, it is also possible to create a picture of a concentration distribution of the substances constituting the living body.

In addition, in an embodiment of the present invention, it is desirable to have an image display part 11 that displays the image information obtained by signal processing. By using the biological information imaging apparatus shown in such an embodiment, it is possible to attain photoacoustic imaging of the deep portion in the living body.

In the following, preferred examples of the present invention will be described.

First Example

As a first example, a simulation was made in which a reflection member having a reflection factor of 100% was used as a reflection member which constitutes part of a biological information imaging apparatus. A case was taken in which light was caused to enter a cube with a side of 4 cm imitating a living body. The simulation calculated a well-known optical diffusion equation by means of a finite element method. For optical constants in the cube, an absorption coefficient was set to 0.1 [$cm^{-1}$], and an effective scattering coefficient was set to 10 [$cm^{-1}$]. A circular-shaped continuous light having a diameter of 1 mm was irradiated to the center of a bottom surface of the cube (the center of a square) at 10 mW. A boundary condition was set such that in the case of the presence of the reflection member, diffused light is totally reflected (a reflection factor of 100%), and in the case of the absence of the reflection member, diffused light substantially totally transmits or passes from and through a boundary (reflection factor of 0%).

Figure 4:
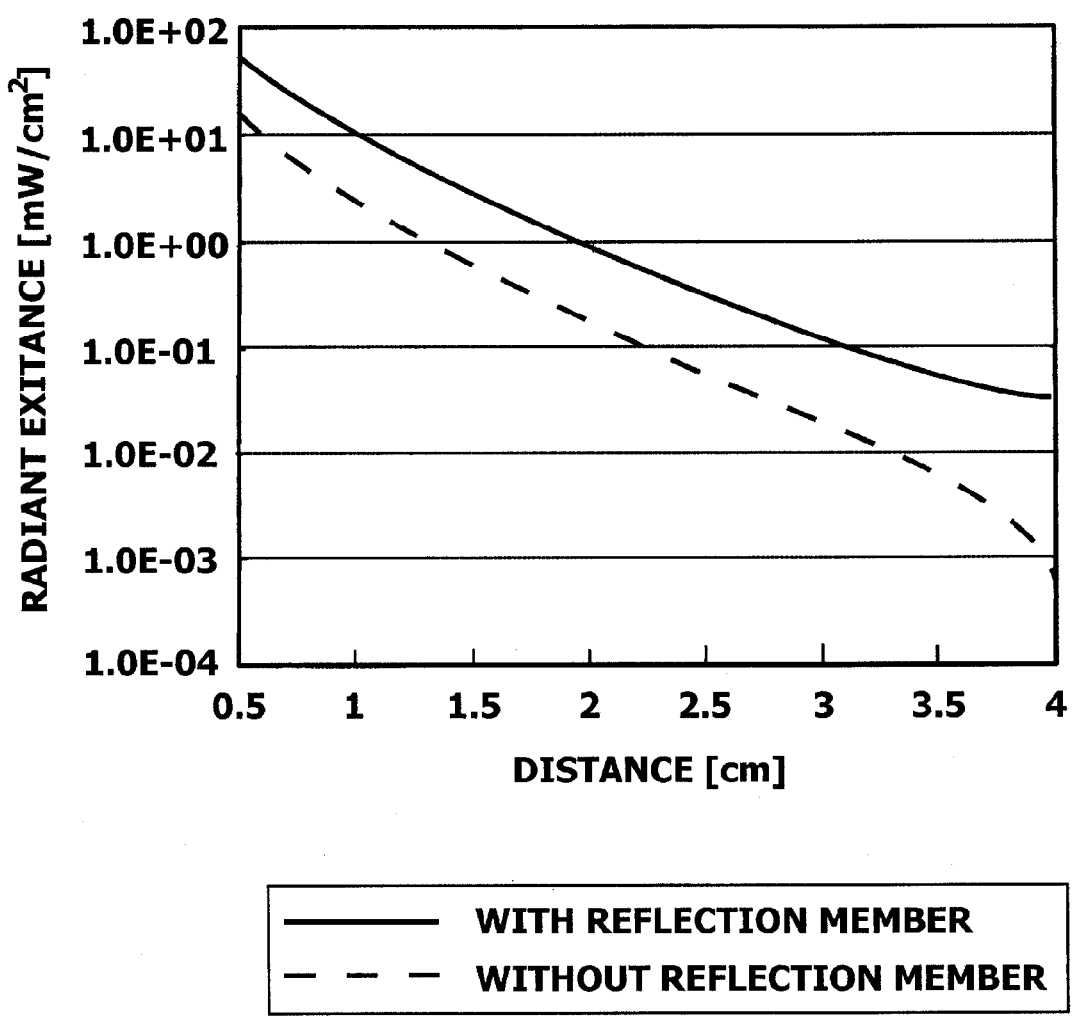
FIG. 4 is a graph in which the radiant exitance [$W/cm^2$] of light is plotted in a depth direction from a light irradiation point at the time of calculating the result by simulation in the case of using a reflection member having a reflection factor of 100% in a first example.

FIG. 4 plots the radiant exitance of light [$W/cm^2$] in a depth direction from a light irradiation point. The radiant exitance of light is the intensity of light integrated over an entire solid angle. The X-axis is the distance from the irradiation point. When the reflection member is arranged around the cube, the radiant exitance of light increases by about 5 times at a depth of 2 cm from the irradiation point, as compared with the case where the reflection member is not arranged.

Second Example

As a second example, a construction example will be described in which the simulated result of the first example is applied to photoacoustic tomography. A signal is acquired which is generated due to a photoacoustic effect by using, as a light source, a YAG laser having a pulse width of 50 nanoseconds and a wavelength of 1,064 nm, and using a specimen with the same optical constants as those of the first example.

In this example, a film of aluminum having a thickness of 10 micrometers is used as a reflection member. Capacitance detection type acoustic wave detectors are used as acoustic wave detectors. At this time, in cases where the light absorber exists in a position at a depth of 2 cm from the irradiation point, a photoacoustic signal emitted from an absorber is greatly increased by using the construction of the present invention, as compared with a conventional case in which a reflection member is not arranged. Alternatively, the strength of an acoustic signal produced from an absorber at a depth of 2 cm in the conventional case where no reflection member is arranged becomes the same as that obtained when the absorber lies at of a depth of about 2.8 cm in the construction of the present invention.

That is, according to the present invention, it becomes possible to obtain the information on the absorber which exists in a position deeper than that in the conventional case.

Third Example

As a third example, construction examples will be described in which a comparison is made between aluminum and gold, which are used as a material of the reflection member, while using a doubled YAG laser (532 nm) in the laser used in the second example. In this example, as a result of the comparison between aluminum and gold which are used as the material of the reflection member, it has become clear that a larger acoustic wave can be obtained by using aluminum rather than by using gold. On the other hand, if a YAG laser of a fundamental wave (1064 nm) is used, a substantially equivalent acoustic wave can be obtained. Accordingly, it is understood that the higher the reflection factor of the reflection member in the wavelength to be used, the more the effect of the present invention can be enhanced.

Fourth Example

Figure 10:
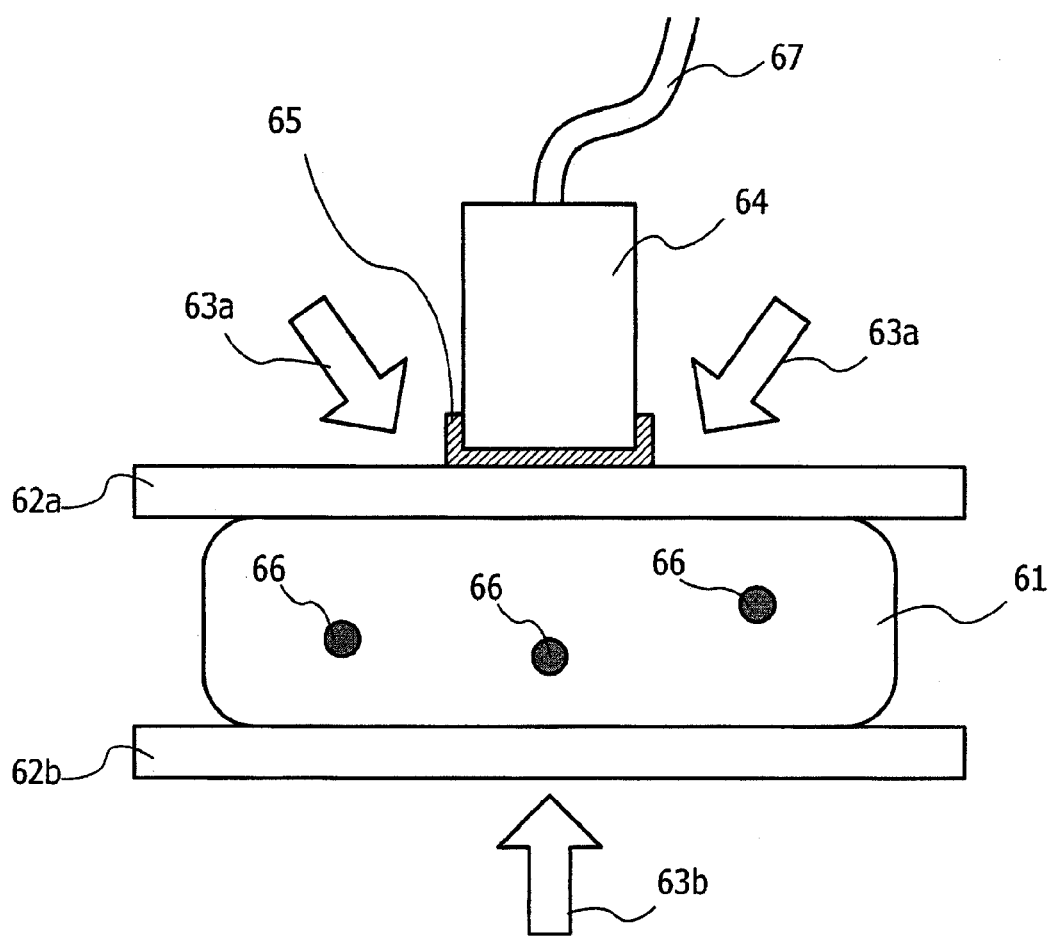
FIG. 10 is a view explaining an example of the construction of a biological information processing apparatus in a fourth example of the present invention.

As a fourth example, a construction example will be described in which the present invention is applied to photoacoustic tomography, referring to FIG. 10.

A living body 61 is fixed by means of a plate 62a made of polymethylpentene and a plate 62b made of an acrylic resin. By using, as a light source, a YAG laser having a pulse width of 50 nanoseconds and a wavelength of 1,064 nm, pulsed lights are irradiated to a living body from opposite sides thereof, as denoted by 63a and 63b. A probe 64 has a two-dimensional array structure in which a receiving element is composed of PZT. The probe 64 has a front face of its measuring plane covered with an aluminum foil 65. The aluminum foil also covers a part of side faces of the probe 64 around the periphery of the measuring plane. The aluminum foil has a thickness of 10 micrometers. Thus, the probe 64 has a receiving region thoroughly covered with a light reflection member in the form of the aluminum foil.

The probe 64 is scanned along the plate 62a made of polymethylpentene in a two-dimensional manner. In addition, the irradiation lights 63a, 63b are also scanned in the same direction as the scanning direction of the probe 64. Thus, the probe 64 detects, while being scanned, a photoacoustic wave produced from alight absorber 66 in the living body 61 by the irradiation lights 63a and 63b being scanned similarly.

The probe 64 converts this photoacoustic wave into an electric signal.

This electric signal is sent to a signal processing part through a signal transmission part 67. In the signal processing part, the electric signal thus transmitted is analyzed, whereby optical property value distribution information in the interior of the living body 61 can be obtained.

Fifth Example

Figure 11:
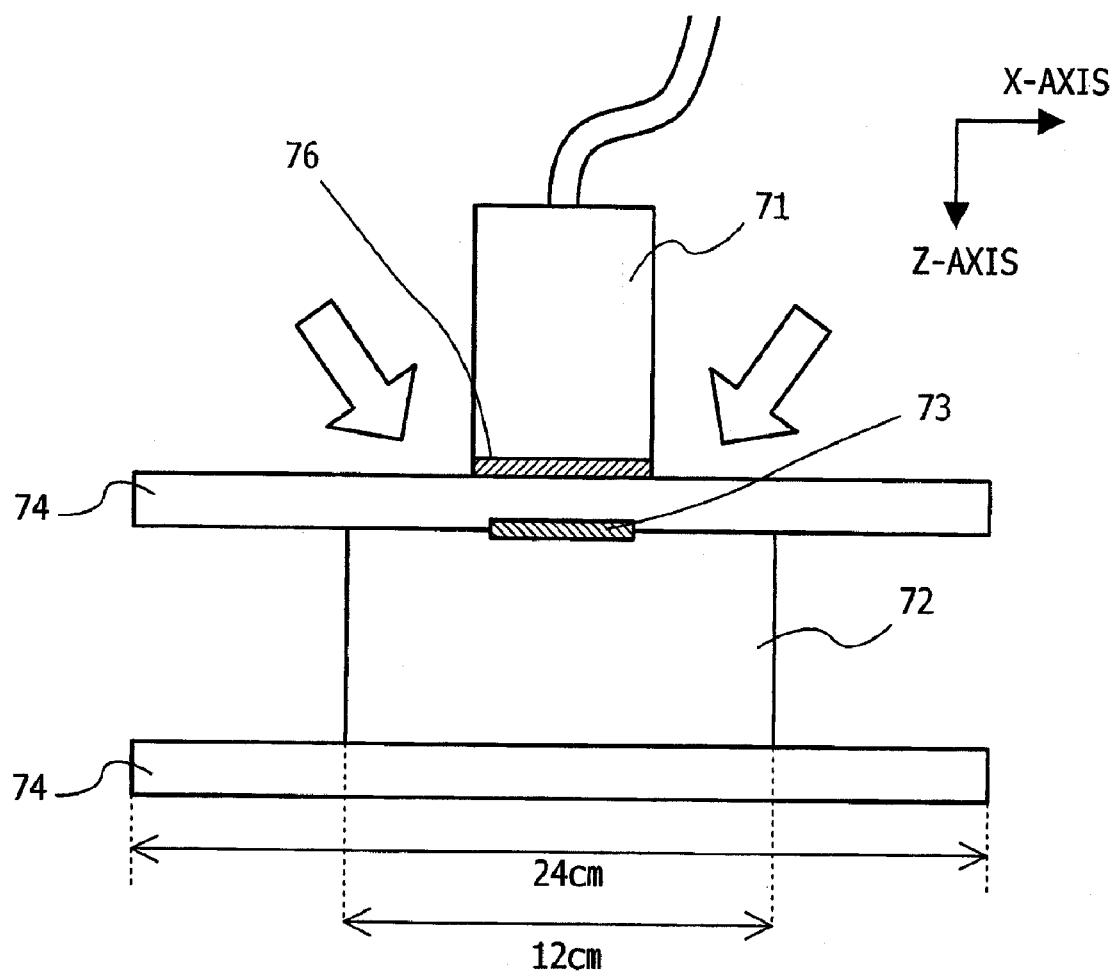
FIG. 11 is a view explaining a simulation model in a fifth example of the present invention.
Figure 12:
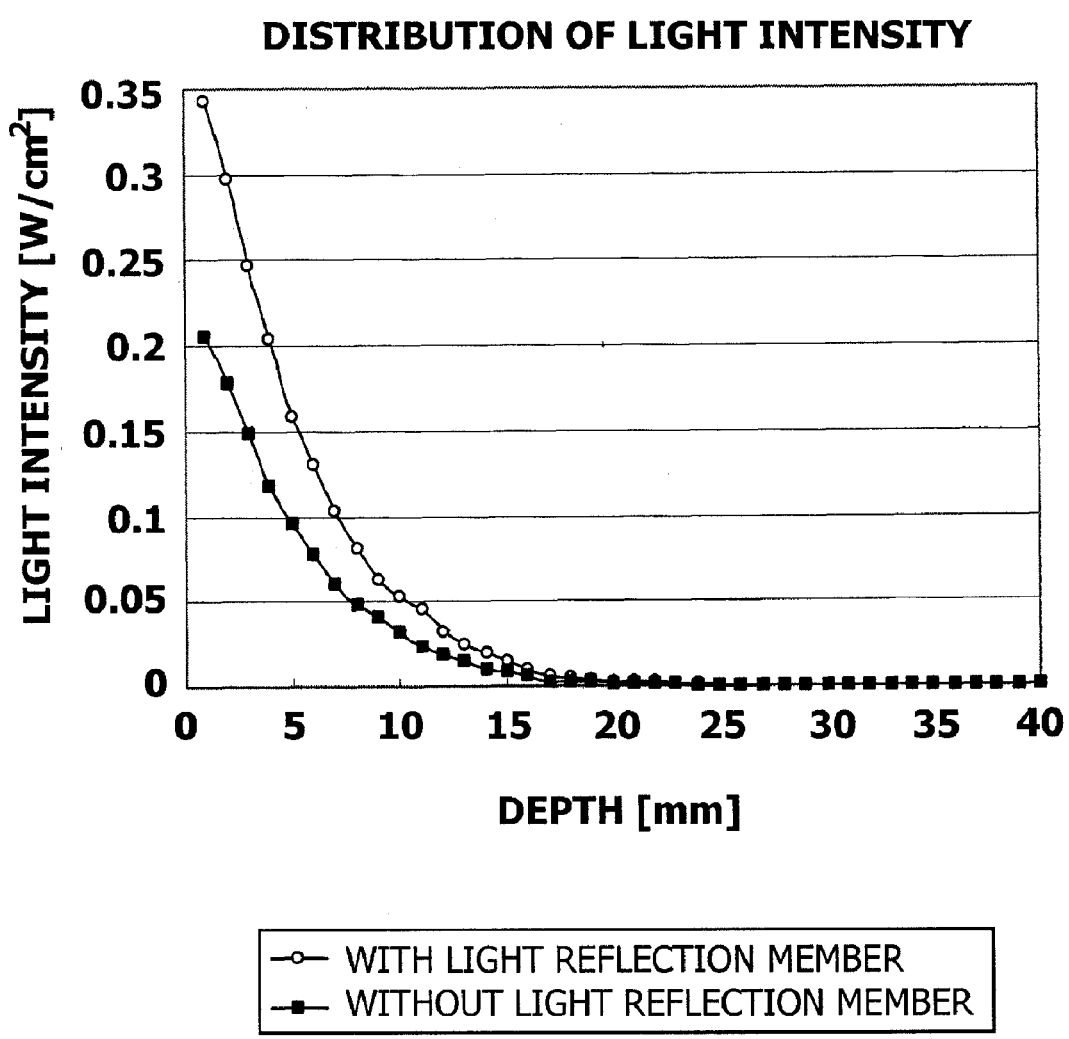
FIG. 12 shows a graph which plots the simulation result in the fifth example of the present invention.

As a fifth example, the increase of light intensity in a living body due to the confinement of light using a light reflection member was simulated. The simulation of light intensity in a specimen 72 was carried out with the use of a simulation model as shown in FIG. 11. A reflection member 76 has a reflection factor of 100%, and a square shape of 2 cm×2 cm. The other construction and respective optical constants in this example are the same as those in the construction of FIG. 8 described in the aforementioned embodiments. Similarly, the simulation of light intensity in the specimen 72 was also carried out in case when the reflection member 76 is not arranged. FIG. 12 plots the radiant exitance of light [W/cm$^2$] in a depth direction from a light irradiation surface 73. The radiant exitance of light is the intensity of light integrated over an entire solid angle. The origin in a depth direction is set to the irradiation surface 73 of the specimen 72. When the reflection member 76 is arranged in a receiving region of the probe 71, the radiant exitance of light increases by about 1.7 times at a depth of 1 cm from the irradiation point, and by about 2 times at a depth of 2 cm from the irradiation point, as compared with the case where the reflection member is not arranged.

Sixth Example

As a sixth example, a construction example will be described in which the simulated result of the fifth example is applied to photoacoustic tomography.

The construction of an apparatus in this sixth example is the same as that of fifth example. A signal is acquired which is generated due to a photoacoustic effect by using, as a light source, a YAG laser having a pulse width of 50 nanoseconds and a wavelength of 1,064 nm, and using a specimen with the same optical constants as those of the fifth example. In this example, a film of aluminum having a thickness of 10 micrometers is used as a reflection member. Capacitance detection type acoustic wave detectors are used as acoustic wave detectors. At this time, in cases where the light absorber exists in a position at a depth of 2 cm from the irradiation point, a photoacoustic signal emitted from an absorber is greatly increased by using the construction of the present invention, as compared with a conventional case in which a reflection member is not arranged. Alternatively, the strength of an acoustic signal produced from an absorber at a depth of 2 cm in the conventional case where no reflection member is arranged becomes the same as that obtained when the absorber lies at of a depth of about 2.8 cm in the construction of the present invention. That is, according to the present invention, it becomes possible to obtain the information on the absorber which exists in a position deeper than that in the conventional case.

As described above, if the present invention is applied, it will become possible to image biological information which exists in a deeper than conventional portion. Here, note that in this example, there has been described an exemplary case in which measurements were made with the living body as a specimen, an object to be inspected or examined of the present invention is not limited to the living body. For example, the present invention can be suitably used for foreign matter inspection for foods, needle inspection for bedding and clothing, and other various non-destructive inspections.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-218104, filed on Aug. 27, 2008, and Japanese Patent Application No. 2009-192233, filed on Aug. 21, 2009, which are hereby incorporated by reference herein in their entirety.

What is claimed is:

1. A photoacoustic apparatus which obtains information on a specimen by receiving photoacoustic waves which are generated from the specimen resulting from light irradiated to the specimen, said apparatus comprising:
a light source for irradiating light to the specimen;
a receiving element for receiving the photoacoustic waves and converting the photoacoustic waves to an electric signal; and
a light reflection member for causing the light, which is radiated out of the specimen, back toward the specimen,
wherein said light reflection member allows the photoacoustic waves to pass therethrough.

2. The photoacoustic apparatus as set forth in claim 1, wherein said light reflection member is arranged in such a manner that an orthogonal projection of said light reflection member onto a light irradiation region to the specimen has a region which overlaps with the light irradiation region.

3. The photoacoustic apparatus as set forth in claim 1, further comprising a plate-shaped member which has a light refractive index of 1.4 or more and which is able to be in contact with the specimen, said plate-shaped member being arranged between said light reflection member and a light irradiation region of the specimen.

4. The photoacoustic apparatus as set forth in claim 3, wherein said plate-shaped member allows photoacoustic waves to pass therethrough.

5. The photoacoustic apparatus as set forth in claim 3, wherein said light reflection member is arranged on said receiving element.

6. The photoacoustic apparatus as set forth in claim 1, wherein said light reflection member has a planar shape.

7. The photoacoustic apparatus as set forth in claim 1, wherein said light reflection member is formed into a concave surface as seen from a specimen side.

8. The photoacoustic apparatus as set forth in claim 5, wherein an area of said light reflection member is larger than an area of a receiving element region.

9. The photoacoustic apparatus as set forth in claim 3, further comprising a movable part for causing said receiving element to scan along said plate-shaped member.

10. A probe which receives photoacoustic waves, said probe comprising: a probe main body having a receiving surface arranged in opposition to the specimen; a receiving element for receiving the photoacoustic waves and converting the photoacoustic waves to an electric signal; and a light reflection member for reflecting the light, which is radiated out of the specimen, back toward the specimen, arranged on a receiving element region, wherein an area of said light reflection member is set larger than an area of said receiving element region, and the light reflection member allows the photoacoustic waves to pass therethrough.

11. The probe as set forth in claim 10, wherein said light reflection member is arranged so as to cover an entire surface of said receiving element region.

12. The probe as set forth in claim 11, wherein said light reflection member also covers a side face of said probe main body.

13. The probe as set forth in claim 10, wherein said light reflection member is larger than said receiving element region, and an aperture for irradiating the specimen with the light introduced from said probe is formed in a part of said light reflection member.

14. The photoacoustic apparatus as set forth in claim 1, wherein said light reflection member has a reflection factor of 80% or more with respect to the light.

15. The photoacoustic apparatus as set forth in claim 1, wherein said light reflection member has a transmittance of 80% or more with respect to the photoacoustic wave.

16. The photoacoustic apparatus as set forth in claim 1, wherein said light reflection member has a thickness of 10 micrometers or less.

17. The probe as set forth in claim 10, wherein said light reflection member has a reflection factor of 80% or more with respect to the light.

18. The probe as set forth in claim 10, wherein said light reflection member has a transmittance of 80% or more with respect to the photoacoustic wave.

19. The probe as set forth in claim 10, wherein said light reflection member has a thickness of 10 micrometers or less.

20. A photoacoustic apparatus which obtains information on a specimen by receiving photoacoustic waves which are generated in the specimen resulting from light irradiated to the specimen, said apparatus comprising: a light source for irradiating light to the specimen; a receiving element for receiving the photoacoustic waves; an acoustic impedance matching member; and a light reflection member, wherein said light reflection member, the acoustic impedance matching member and the receiving element are arranged in that order from the side of the specimen.

21. The probe as set forth in claim 10, further comprising a member having a light refractive index of 1.4 or more,
wherein said member having the light refractive index of 1.4 or more, said light reflection member and said receiving element are arranged in that order from side of the specimen.

22. The photoacoustic apparatus as set forth in claim 20, further comprising a member having a light refractive index of 1.4 or more, wherein said member having the light refractive index of 1.4 or more is arranged at the side nearer to the specimen as compared with said light reflection member.

23. The photoacoustic apparatus as set forth in claim 20, wherein said light reflection member is formed into a concave surface as seen from a specimen side.

24. The photoacoustic apparatus as set forth in claim 20, wherein an area of said light reflection member is larger than an area of a receiving element region.

25. The photoacoustic apparatus as set forth in claim 22, further comprising a movable part for causing said receiving element to scan along said member having the light refractive index of 1.4 or more.

26. The photoacoustic apparatus as set forth in claim 20, wherein said light reflection member has a reflection factor of 80% or more with respect to the light.

27. The photoacoustic apparatus as set forth in claim 20, wherein said light reflection member has a transmittance of 80% or more with respect to the photoacoustic waves.

28. The photoacoustic apparatus as set forth in claim 20, wherein said light reflection member has a thickness of 10 micrometers or less.

29. A probe which receives photoacoustic waves which are generated from a specimen, said probe comprising: a receiving element which receives the photoacoustic waves and converts the photoacoustic waves into electric signals; an acoustic impedance matching member; and a light reflection member, wherein said light reflection member, said acoustic impedance matching member and said receiving element are arranged in that order from the side of the specimen.

30. The probe as set forth in claim 29, further comprising a member having a light refractive index of 1.4 or more, wherein said member having the light refractive index of 1.4 or more is arranged at the side nearer to the specimen as compared with said light reflection member.

31. The probe as set forth in claim 29, wherein said light reflection member is arranged so as to cover an entire region of said receiving element.

32. The probe as set forth in claim 31, wherein said light reflection member also covers a side face of a main body of the probe.

33. The probe as set forth in claim 29, wherein said light reflection member has a reflection factor of 80% or more with respect to the light.

34. The probe as set forth in claim 29, wherein said light reflection member has a transmittance of 80% or more with respect to the photoacoustic waves.

35. The probe as set forth in claim 29, wherein said light reflection member has a thickness of 10 micrometers or less.

* * * * *